United States Patent [19]
Anbar

[11] Patent Number: 5,272,340
[45] Date of Patent: Dec. 21, 1993

[54] INFRARED IMAGING SYSTEM FOR SIMULTANEOUS GENERATION OF TEMPERATURE, EMISSIVITY AND FLUORESCENCE IMAGES

[75] Inventor: Michael Anbar, Snyder, N.Y.

[73] Assignee: Amara, Inc., Snyder, N.Y.

[21] Appl. No.: 953,990

[22] Filed: Sep. 29, 1992

[51] Int. Cl.$^5$ .................... G01N 21/64; G01N 25/00
[52] U.S. Cl. .................... 250/332; 250/330; 250/339; 250/458.1; 374/9; 364/557
[58] Field of Search ............ 250/339, 458.1, 332, 250/330; 364/557; 374/9, 121, 124

[56] References Cited

U.S. PATENT DOCUMENTS

| | | | |
|---|---|---|---|
| 4,880,314 | 11/1989 | Kienitz | 364/557 |
| 4,974,182 | 11/1990 | Tank | 250/339 |
| 5,099,121 | 3/1992 | Allen | 250/339 |

OTHER PUBLICATIONS

Anbar, et al.; "Scope and Limitations of Imaging Using Multiwavelength Infrared Detection"; Optical Engineering (Oct., 1992) (First published Nov., 1991).

*Primary Examiner*—Carolyn E. Fields
*Attorney, Agent, or Firm*—Sommer, Oliverio & Sommer

[57] ABSTRACT

The present invention comprises a method and apparatus for determining actual temperature, reflectivity and fluorescence of a surface and comprises in the preferred embodiment a two-dimensional focal plane array of rapidly tunable infrared detectors, 11, adapted to detect the emitted infrared flux from a surface of interest, 10, across pre-selected spectral segments in the 4–15 μm range. The invention further comprises a computer having deconvolution algorithms, 13, for isolating the effects of reflectivity, fluorescence and environmental factors affecting infrared emission for each pixel of the generated image at various spectral segments in the 4–15 μm range. The device further includes means for generating images of temperature, emissivity and fluorescence for diagnostic use. The preferred embodiment of the invention also contemplates the use of thermostated black body reference emitters, 12, at the edges of the field of view for enhancing and speeding deconvolution of the detected data across the 4–15 μm spectrum.

17 Claims, 3 Drawing Sheets

INFRARED IMAGING SYSTEM FOR SIMULTANEOUS GENERATION OF TEMPERATURE, EMISSIVITY AND FLUORESCENCE IMAGES

TECHNICAL FIELD

The present invention relates generally to the field of infrared detection cameras and, more particularly, to a rapidly tunable infrared flux detector and imaging system adapted to detect the amount of infrared flux in narrow bands across the infrared spectrum of interest and further, the use of the spatial distribution of detected infrared flux to assess true temperature, as well as emissivity and fluorescence. Such an imaging system is particularly useful in clinical diagnosis and management of skin and other disorders.

BACKGROUND OF THE INVENTION

I. General Detection Systems and the Problem

Infrared imaging or detection is anticipated to be a useful aid in the diagnosis and management of various diseases or clinical pathologies indicated by temperature variations of the skin. For example, it is thought that infrared detection and assessment of true skin temperature may be an important diagnostic and curative tool in the treatment of malignancies, burns, wounds to the skin and also, to measure and perfect the use of topical treatments absorbed through the skin.

On account of the characteristics of the skin and the strict requirements of accurate measurement of absolute skin temperature for diagnosis and management, a relatively artifact-free system is needed to detect and measure the key parameters for effective clinical application of the concept; i.e., accurate measurement of absolute skin temperature, emissivity and fluorescence.

The currently available infrared imaging and sensing systems adaptable for clinical use, both economically and scientifically, typically measure infrared flux over a single band of the infrared spectrum somewhere between 8 and 12 $\mu$m. These systems estimate the temperature of an image (e.g., an area of interest on the skin) by comparing the amount of infrared flux detected with that emitted by an ideal "black body" emitter at a known temperature. This technique assumes, of course, that the skin, in the 10 $\mu$m range, is not reflective (or fluorescent) and accordingly, has an emissivity equal to that of an ideal "black body."

This is clearly not the case. Skin emissivity is somewhat less than 100% in a normal state, and the skin can become even more reflective if treated with topical agents or if exposed to extraneous light or other environmental conditions. In addition, conditions exist where the skin becomes fluorescent thereby emitting infrared flux in excess of that of an ideal "black body" at a specific wavelength.

The skin, as well as being affected by topical agents or disease, also changes spectral characteristics through interaction with visible and infrared radiation from other sources in the clinical laboratory or surrounding clinical environment. Accordingly, still further aberrations occur in the "black body" comparison now used to estimate skin temperature.

On account of these aberrations, the "black body" comparison is inadequate for medical diagnosis and management. In addition, single parameter corrections of skin temperature are also not appropriate since the reflectivity of the skin is wavelength dependent unlike that of the "gray body." Further, reflectivity of the skin is associated with artifacts related to environmental infrared emissions.

It is important, therefore, to determine absolute temperature, fluorescence and emissivity (or reflectivity) because these parameters and the relationships among them may be quantifiable and related to certain pathologies or important clinical applications. In short, if one can accurately measure of fluorescence and reflectivity in the infrared 10 $\mu$m band, one can then accurately calculate and assess temperature through the use of a corrected "black body" calculation and comparison.

II. Prior Art Systems

To determine temperature, reflectivity and fluorescence which are dependent upon the environmental radiation in the infrared and visible regions, one needs simultaneous measurement of the infrared flux at 5 or more bands of the infrared spectrum. Further, this measurement must be done fast (i.e., at a rate faster than a frame per second).

The most common and simple form of detection system comprises a single detector of a known and constant wavelength band onto which each unit area of the object is consecutively focused by a set of rapidly moving mirrors. In the single detector system, each pixel of the image is detected and processed separately in series. Accordingly, in order to obtain an image having a resolution of 256×256 pixels in one second, the focusing optics of the single detector must insure that each pixel is scanned in $1/256^2$ of a second. This, of course, places tremendous burdens on the detectors, electronics and the mechanics of the focusing apparatus and makes this system ineffective.

Multiple detector systems are also known in the prior art. The typical multiple detector system has 64, 128 or 256 detectors arranged in a linear array. Accordingly, the multiple detector system "reads" an entire line of pixels at once. To detect an image of 256×256 pixels, the focusing optics must be adapted to refocus the detectors once per second.

It is also known to arrange detectors in a focal plane array of 256×256 wherein each pixel of the image is read by a separate detector and the detected data is multiplexed. This system has two important advantages: first, it has no moving parts that may wear or become misaligned and second, the data, accumulated in parallel, is read off electronically like in a conventional CCD video camera facilitating data accumulation at a fast rate (30 to 300 frames per second).

Each of the detection systems set forth above comprise detectors having identical infrared responsivity characteristics. Multiple detector systems (e.g., stacked systems) have been devised wherein each pixel is scanned over discrete and different bands in the infrared spectrum; e.g., two separate infrared bands may be detected. Calculation of the ratios between various detected values at different wavelengths are then compared to the expected value from an ideal "black body" emitter to estimate temperature. The "stacked" two-band detector system, however, is insufficient to yield the minimum 5 bands required for determining temperature, emissivity and fluorescence. The technology of "stacking" detectors is unlikely to produce a practical 5 layer detection system in the future.

Another way to measure infrared flux in different wavelength bands is to use an array of different detectors and focus each point of the object on each of the detectors by a set of rotating mirrors. This system is even slower than the single detector scanning system and is susceptible to optical aberration and parallax.

While these techniques disclose deviations of the surface of interest from a true "black body," the techniques are ineffective for isolating the deviation or the reason therefor (i.e., the effects of reflectivity or fluorescence) on account of the wide width of the detected bands.

III. Proposed Solution

There is a current need for an infrared detection system for clinical use that will accurately and simultaneously assess absolute temperature, fluorescence and emissivity (or reflectivity) of an area of skin or other biological samples. To accomplish this goal, the imaging system must be capable of detecting infrared flux at various wavelengths for each pixel across the surface of interest.

Because of the costliness and attendant problems of multiple detector systems, the preferable system would comprise a single detector, arranged in a two-dimensional array, adapted to be modulated over wavelengths in the 5 μm through 15 μm range. Modulated single detectors can be arranged in a two-dimensional focal plane array thereby insuring efficient and accurate measurements of multiple values for each pixel of an image.

While an ideal imaging system would produce photon flux values across the full spectrum of infrared for each pixel, it is presently impossible to accomplish this goal efficiently and at a reasonable cost. The present invention, therefore, contemplates an imaging system adapted to adduce the spatial distribution of emissivity, true temperature and fluorescence over an area of interest by detecting changes in infrared flux across the 4 μm to 15 μm band as the spectrum is scanned with a "window" of known shape. The detected values may, through the use of known ratio analysis and deconvolution algorithms, be compared with the expected results for an ideal "black body" emitter. Those results, across a modulated narrower band, permit the isolation of the reason for any deviation from the ideal "black body" emitter across the 4-15 μm spectrum (i.e., deviations caused by fluorescence or reflectivity) which, in turn, enables the imaging system to function as a precise diagnostic tool without the aberrations or errors present in previous systems and to identify absolute temperature of the skin or other biological samples.

DISCLOSURE OF THE INVENTION

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

The present invention generally provides an apparatus and method for determining actual temperature, fluorescence and reflectivity (1−emissivity) of a surface, e.g., skin, from the detected distribution of infrared emissions across the 4–15 μm region of the surface of interest. From the detected values of emitted infrared flux, the invention contemplates the use of a computer and attendant algorithms to deconvolute the actual values of temperature, reflectivity and fluorescence of the surface by solving a series of simultaneous equations expressing the relationship among the variables and the infrared flux emitted from an ideal "black body" at a known temperature.

The invention further contemplates the generation of pictorial or graphic images of the distribution of temperature, fluorescence and reflectivity across the surface as an aid for determining pathology or the presence of injury or disease commonly associated with variations in actual skin temperature, reflectivity and fluorescence.

The preferred embodiment of the invention is adapted to detect infrared emissions in the 4-15 μm range from a surface of interest (e.g., 10) such as an area of skin. The preferred embodiment includes a two-dimensional array of multiple wavelength infrared detectors (e.g., 11) generally of array size of 256×256, the responsivity of which can be continuously modulated. These detectors are adapted to be focused on the surface of interest.

Each detector of the array is adapted to detect infrared flux emitted from a single and separate area of the surface and represent it in a single pixel. Accordingly, a resolution of 256×256 pixels is achieved. Similarly, each detector is modulated to scan and detect infrared emissions of the designated area across narrow, preselected band segments in the 4-15 μm range, each of such segments having a band width of between 1 and 3 μm. Accordingly, the infrared emissions detected from each area comprise multiple values across each of the pre-selected segments of interest.

The invention further contemplates in its preferred embodiment, the use of a computer and attendant algorithms (e.g., 12) adapted to receive the detected data for each pixel in parallel from each of the detectors. Since it is known that the relationship among actual temperature, reflectivity and fluorescence is a function of five variables; i.e.;

$E(T_b)$ Emission of an ideal "black body" emitter which is a function of its temperature, $T_b$ $\epsilon(\lambda_e)$ Emissivity of the surface at issue which is a function of wavelength $E(T_{en})$ Infrared emission of the surrounding environment which is a function of its temperature ($T_{en}$)

$\lambda_{en}$ Wavelength distribution of light of the environment that might induce fluorescence $E(\lambda_f)$ Emission of infrared fluorescence changing with wavelength. Since the wavelength distribution of "black body" emissions is known, it is possible to iteratively solve for the values of temperature, fluorescence and reflectivity through a series of at least five equations or algorithms. Hence, a minimum of five segments of infrared emissions for each pixel must be detected; however, it is anticipated in the preferred embodiment that up to 12 pre-selected band segments will be measured thereby yielding optimum data for efficient and accurate calculation of the parameters of temperature, reflectivity and fluorescence.

The invention further contemplates the generation of separate images (e.g., 13) for temperature, reflectivity and fluorescence for the surface of interest thereby providing a pictorial view of aberrations in skin or surface temperature, reflectivity and fluorescence for use in diagnosis or management in a clinical setting. Moreover, since detection is continuously modulated, the generated image may be similarly made time-dependent.

The preferred embodiment provides that each of the detectors is rapidly tunable across the pre-selected segments; however, another embodiment of the invention provides for modulation through the use of a planar array of wide band detectors (e.g., 11) in series with a notch or pass filter (e.g., 15) and focusing optics (e.g., 19) to achieve the desired modulation over the pre-selected segments of 1-3 $\mu$m in width absent an economical or feasible rapidly tunable detector system.

The modulating filters are well known in the art and may comprise, for example, an acousto-optical filter or a rotatable multi-sector set of interference filters (e.g., 16).

Similarly, to further enable expediency of calculation, the invention contemplates the use of ideal "black body" emitters (e.g., 12) positioned at the of the field of view and adapted to emit a known infrared value for a given temperature. The use of reference "black body" emitters provides an iterative starting point for calculation of temperature, fluorescence and reflectivity for the area of interest.

Through the use and accumulation of the distribution of infrared flux emitted by the surface of interest across the pre-selected narrow bands of the 4–15 $\mu$m spectrum, the apparatus and method of the invention enables aberrations from the ideal "black body" to be isolated and accounted for, thereby resulting in an accurate measurement of absolute temperature of the surface of interest (e.g., skin). Therefore, the present system provides an artifact-free determination of temperature without the error and inaccuracy of the previous "black body" estimates of surface or skin temperature that fail to account for the less than perfect emissivity of skin, as well as environmental factors that determine the reflectance and fluorescence of the skin or other biological samples in its normal state.

Accordingly, an object of the invention is to provide a method and apparatus for determining actual skin or surface temperature, as well as fluorescence and reflectivity.

Still another object of the invention is to provide a method and apparatus for determining actual skin temperature more accurately than the "black body" comparison methods of the prior art.

Another object of the invention is to provide a method and apparatus for detecting actual skin temperature that is readily adaptable to clinical use and for the diagnosis of certain pathologies and disease.

Another object of the invention is to provide a method and apparatus for detecting actual skin temperature, reflectivity and fluorescence that is computationally efficient and accurate.

An additional object of the invention is to determine the true temperature of a biological specimen and from that assess the viability of the living cells that constitute it.

Yet another object of the invention is to measure the changes in time of temperature, emissivity and fluorescence, which can provide information about the pathosphysiology of skin temperature regulation and/or changes associated with absorption and excretion of drugs, toxic agents, nutrients and the like by the skin.

These and other objects of the invention are and will become apparent from the previous portions of the specification and from the following drawing figures and claims.

MODES OF CARRYING OUT THE INVENTION

The present invention comprises a method and apparatus for determining temperature, reflectivity and fluorescence of a surface, e.g., human skin, from the detection of emitted infrared flux and the measurement of the distribution of such infrared flux across the 4–15 $\mu$m wavelength spectrum. The invention contemplates the measurement of infrared flux across the 4–15 $\mu$m spectrum in pre-selected incremental narrower band segments to provide an accurate measure of the distribution of emitted infrared flux for each pixel of the surface image. The present invention seeks to improve upon the detection systems known in the art which, in part, comprise single detectors or multiple detector systems adapted to measure infrared flux across a single wavelength band of wide response width and accordingly, are ineffective for the accurate measurement of actual temperature, fluorescence and reflectivity of a surface of interest.

Figure 3A:
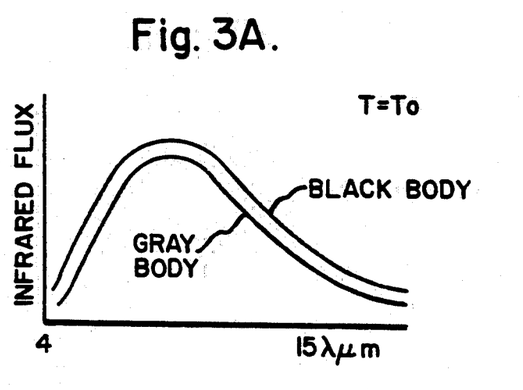
FIG. 3A is a graphic representation of the infrared flux emissions of an ideal "black body" and a "gray body" across the 4–15 $\mu$m spectrum.

As depicted in FIG. 3A, Planck's Law describes the relationship between the infrared flux emitted from an ideal "black body" across the infrared spectrum for a constant known temperature. The relationship results in the generation of a family of curves for various temperatures showing the value of electromagnetic radiated flux for wavelength values in the 0.1 to 100-plus μm region. Planck's law is, of course, well-known to one of ordinary skill in the physical sciences. So too are the characteristics of the curves generated by Planck's Law and the equations that derive the graphical relationships.

Using Planck's Law and the generated family of curves as a starting point, and assuming the ideal "black body" of Planck's Law is a 100% emitter, the emissivity of other surfaces, such as human skin, are expressed as a ratio of their emitted infrared flux to the infrared flux emitted by an ideal "black body" as described by Planck's Law at various temperatures. Human skin, for example, has an emissivity of approximately 95% in the 10 μm range. Skin can be reflective and fluorescent depending upon environmental, topical or pathological factors. Accordingly, calculation of actual skin temperature through comparison of infrared emissions over the 4–15 μm range with that of an ideal "black body" suffers from inaccuracies attendant to the deviation of the emissivity of skin when compared to that of an ideal "black body." Moreover, any such comparison also suffers from a failure to account for the cause of the resulting deviation or inaccuracy; i.e., the reflectivity, fluorescence or environmental factors affecting the infrared emission of the biological sample of interest.

Continuing to advert to FIG. 3A, the "gray body" curve interposed below that of the ideal "black body" does not result in an accurate or even better estimate of the characteristics of human skin, nor is the "gray body"curve able to account for or isolate the causes of deviations or variations of skin temperature determined from a comparison of emitted infrared flux with that of the "gray body" emitter. It is readily apparent from FIG. 3A and is well-known in the art that a "gray body" emits infrared flux in an amount less than that of an ideal "black body" but with a resulting relationship parallel to the "black body" curve. In short, emissions of a "gray body" when compared to that of an ideal "black body" emitter are not wavelength dependent. Since the reflectivity of the skin, however, is wavelength dependent, the "gray body" approximation is ineffective for determining actual temperature of the skin.

Figure 3B:
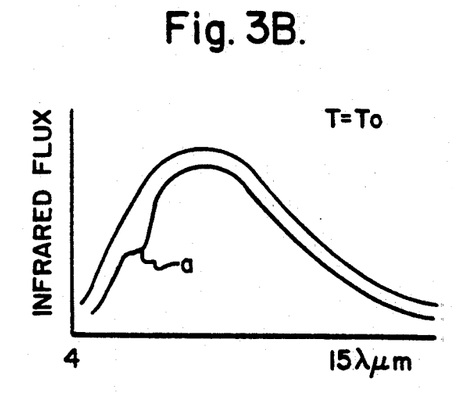
FIG. 3B is a graphic representation of the emitted infrared flux of an ideal black body and a surface exhibiting reflectivity only in a limited band in the 4–15 $\mu$m range.

FIGS. 3B–E better illustrate the behavior of human skin. For example, FIG. 3B graphically depicts the ideal "black body" curve generated by Planck's Law at a temperature equal to $T_O$ and imposed thereunder, the curve emitted for a representative surface such as the human skin in the 4–15 μm range. FIG. 3B further depicts at point "a," a "dip" in infrared emission from the normal curve. This decrease in infrared emission is indicative of reflectivity at the indicated wavelength.

Figure 3C:
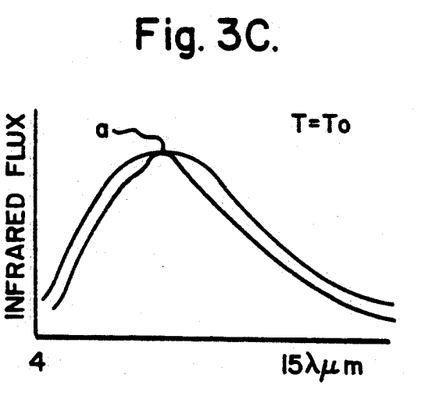
FIG. 3C is a graphic representation of the emitted infrared flux of an ideal black body and a surface exhibiting 100% emissivity only in a limited band in the 4–15 $\mu$m range.

Similarly, FIG. 3C illustrates at point "a," where a surface such as human skin is, in fact, 100% emissive and approaches that of an ideal "black body" emitter, demonstrating an increase in emitted flux.

Figure 3D:
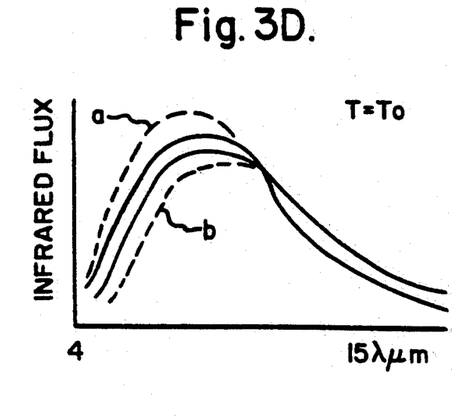
FIG. 3D is a graphic representation of the infrared emission of an ideal black body and a partially reflective surface showing the effects of environmental temperature, both warm and cold, in the 4–15 $\mu$m range.

FIG. 3D illustrates the effect of environmental factors, especially environmental temperature, relevant to the emission of skin. A curved region "a" illustrates increased emission in excess of that of an ideal "black body" emitter which would generally be indicative of a higher environmental temperature reflected by the skin, while a point "b" shows reduced infrared emission indicative of reflected colder environmental conditions.

Figure 3E:
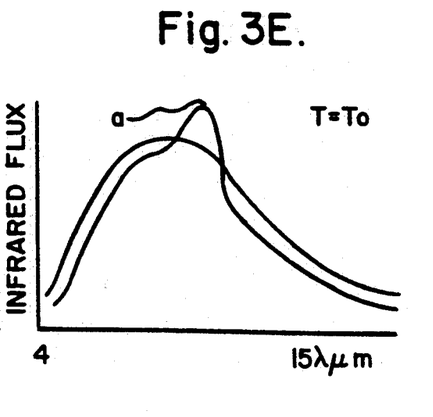
FIG. 3E is a graphic representation of the comparison of an ideal black body and a surface exhibiting fluorescence in a limited band in the 4–15 $\mu$m range.

Finally, FIG. 3E describes the presence of increased infrared emissions in excess of that emitted by an ideal "black body" at point "a" indicative of fluorescence at the indicated wavelength.

FIGS. 3B–E graphically illustrate the deviations from ideal "black body" behavior typically exhibited by the human skin; i.e., wavelength and temperature dependent reflectivity, fluorescence and environmental factors. Accordingly, the present invention provides a method and apparatus for determining actual skin (or other surface) temperature, reflectivity and fluorescence by accounting for deviations from the ideal "black body" emitter curves of Planck's Law attributable to the characteristics of the emitting surface and related environmental factors over the infrared band of interest.

The present invention is adapted to isolate the "artifacts" present in the emissivity curves at various temperatures of a surface of interest by determining the emitted infrared flux in narrower (i.e., 1–3 μm) band widths across the infrared spectrum between 4 and 15 μm for each pixel of a surface image. A distribution of the emitted infrared flux across five or more (preferably 12) segments of the 4–15 μm band provides for the deconvolution of aberrations in the infrared emissions from that of an ideal "black body" and accordingly, accurate calculation of actual temperature, reflectivity and fluorescence of, for example, human skin.

Figure 1:
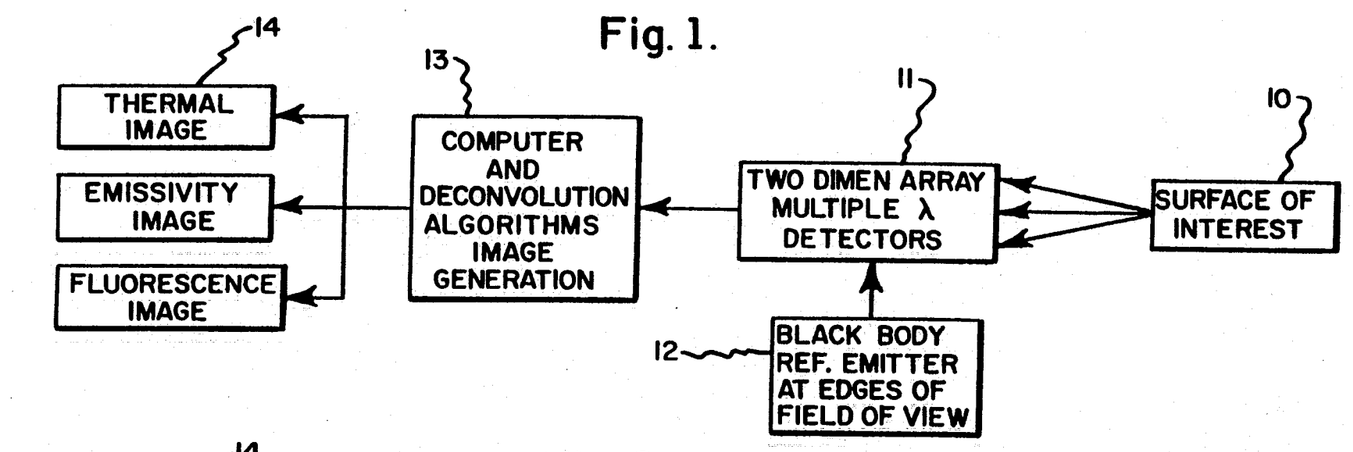
FIG. 1 is a graphic representation of the invention of the invention in black box form showing each of the components and steps thereof.

Turning to FIG. 1, the components of the apparatus comprising the invention are illustrated in flowchart or "black box" form. In particular, the preferred embodiment of the invention operates on a surface of interest (e.g., an area of skin), 10. A two-dimensional focal plane array of multiple wavelength infrared detectors, 11, are arranged in an array of, e.g., 256×256. Ideal "black body" reference emitters, 12, are interposed along the edges of the field of view to provide a starting point for the iterative deconvolution of the detected infrared distribution for purposes of calculating temperature, fluorescence and reflectivity (1 − emissivity).

Figure 5:
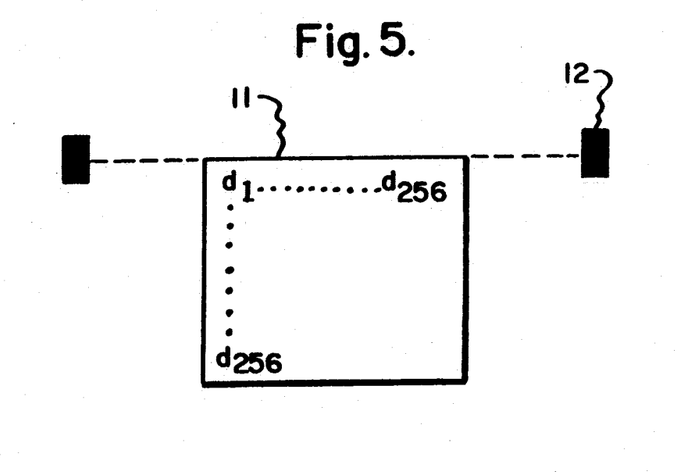
FIG. 5 is a schematic representation of the two-dimensional focal plane array of detectors.

FIG. 5 demonstrates, in schematic form, the array of detectors, for example, (D1 ... D256) and the positioning of the "black body" reference emitters, 12. Each of the detectors is arranged to detect the infrared emissions of a single area of the object of interest and accordingly, the detected infrared flux for each area is simultaneously accumulated by each of the detectors. Unlike single detector systems or linear array systems, both well known in the art, the two-dimensional focal plane array configuration of the present apparatus obviates the use of mechanical and inefficient refocusing means to capture the required flux from each sub-area of the image quickly enough to insure an accumulation of data sufficient to provide an accurate image.

Each of the detectors is a modulated multiple wavelength infrared detector and accordingly, the array is configured to scan each pixel over pre-selected narrow segments of prescribed band width, namely from 1–3 μm in the preferred embodiment of the invention. Modulation of the band width segments over the 4–15 μm range results in the detection of a series of infrared flux readings, one for each pre-selected modulated band width, and comprises a distribution of the infrared flux emitted by the surface of interest for each pixel of the image in the total 4–15 μm band. For example, the preferred embodiment contemplates modulation through a range of 12 pre-selected narrow band width segments and accordingly, each detector is adapted to provide 12 separate values for each designated pixel of the image of the infrared flux in the segments.

Since the actual temperature, reflectivity and fluorescence of a surface such as skin can be calculated from algorithms or simultaneous equations well-known in the art involving five variables, the number of pre-selected spectral segments must be at least five; i.e., one measured value for each unknown. In the preferred embodiment, 12 segments are pre-selected and measured thereby insuring an efficient and accurate deconvolution of the relationships among the variables to determine actual temperature, fluorescence and reflectivity as a function of wavelength, environmental temperature, wavelength distribution of the environmental emissions, wavelength of the photons exciting fluorescence and black body wavelength distribution.

The preferred embodiment contemplates the use of detectors that are rapidly tunable over the pre-selected band segments. An example of a rapidly tunable detector adapted to be configured in focal plane array is the known Putley detector that quantizes free electron levels by an externable controllable magnetic field requiring liquid helium temperature to overcome noise. The preferred embodiment of the invention contemplates use of the Putley detector as the best known continuously tunable infrared detector system currently available. The invention, however, contemplates use of any improved tunable systems that may emerge in the future and that may be adapted for clinical use.

Continuing to advert to FIG. 1, the preferred embodiment of the invention contemplates the generation of images displaying the distribution and values of actual temperature, emissivity and fluorescence, 14, through the use of an image generation means such as a software program and screen or printer made a part of the computer system, 13, for displaying the data in a usable form.

Figure 2:
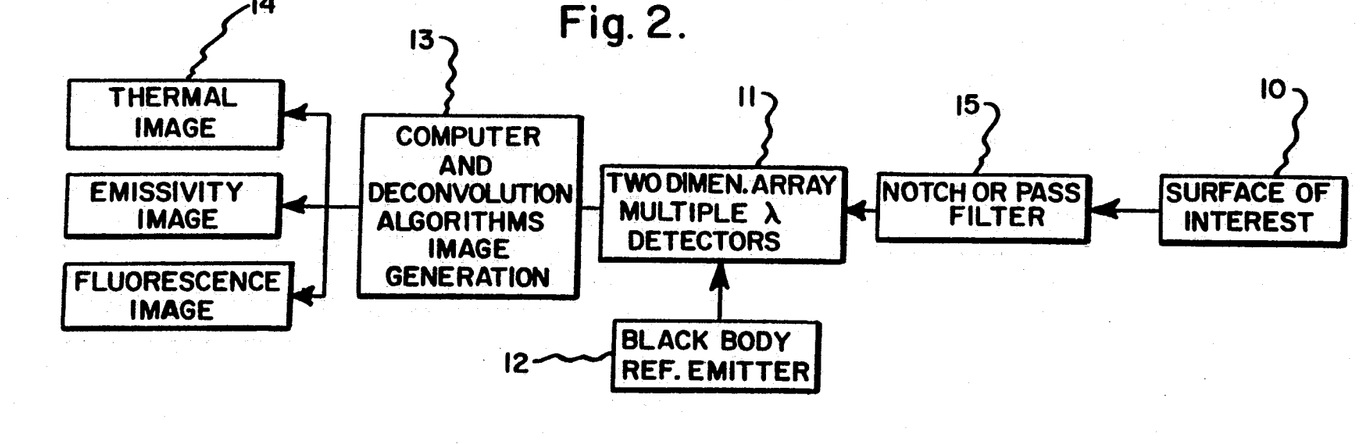
FIG. 2 is a graphic representation of another embodiment of the invention in black box form showing each of the components and steps thereof.

Another embodiment of the invention is disclosed in block diagram form in FIG. 2. In particular, this embodiment contemplates the use of a two-dimensional focal plane array of infrared detectors modulated across the pre-selected spectral segments of interest through the use of a notch or pass filter 15 in series between the surface of interest, 10, and the detector array, 11.

Figure 6:
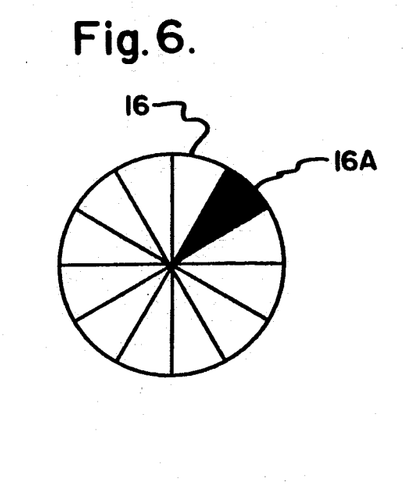
FIG. 6 is a schematic diagram of a rotatable segment notch filter.

The infrared detectors comprising the two-dimensional array, rather than being modulated in the narrow pre-selected band segments through rapid-tuning as in the preferred embodiment, are wide band detectors modulated through the use of the band pass or notch filter such as an acousto-optical tunable filter or simple rotary multi-sector filter, 16, having, e.g., segments of interest, 16A, as shown in FIG. 6. Use of a pass or notch filter to modulate a wide band detector is well-known in the art, and many different filters may be employed to achieve the result of modulation across the pre-selected narrow segments. The wide band detector in this embodiment of the invention comprises an HdCdTe detector adapted to detect infrared in the 4–15 μm spectral band. GaAs/AlGaAs quantum well detectors could also be used. The use of the filter, 16, however, results in modulation and detection of infrared emitted in 1–3 μm bands of at least 5 in number and preferably 12 as in the preferred embodiment of the invention.

Continuing to advert to FIG. 6, this embodiment of the invention includes attendant components identical to those of the preferred embodiment such as the computer system and deconvolution algorithms, 13, and generated temperature, emissivity and fluorescent spatial distribution images, 14. For ease of calculation, the embodiment of the invention also includes thermostated reference "black body" emitters, 12, at the edges of the field of view.

Figure 4:
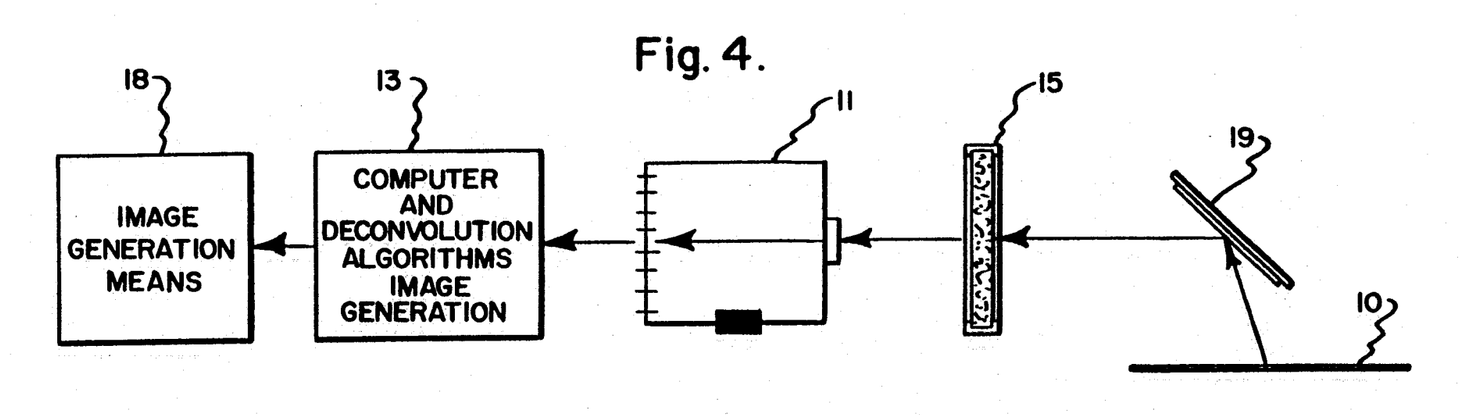
FIG. 4 is a schematic diagram of the apparatus comprising the invention.

In addition, FIG. 4 illustrates the apparatus of the second discussed embodiment and includes the use of focusing optics such as a mirror, 19, to direct the emitted infrared flux through filter 15 and to detector array 11. Such focusing optics may also be incorporated into the preferred embodiment of the invention.

Accordingly, the second embodiment of the invention contemplates the use of a band or notch filter to modulate the well-known wide band detectors of the art, rather than the use of the more expensive and complex rapidly tunable detectors also known in the art. In either instance, however, the devices operate essentially in the identical manner.

Accordingly, in operation, the surface of interest is scanned across at least 5 and preferably twelve 1–3 μm pre-selected segments of interest in the 4–15 μm range and the emitted infrared flux is detected by each of the arrayed detectors for each sub-area of the object. This collected data, in parallel, is transferred to a computer having deconvolution algorithms for determining actual temperature, fluorescence and reflectivity from the various detected flux values at each of the pixels of the image across the 1–3 μm spectral bands, thermostated "black body" reference emitters are included at the edges of the field of view to enhance and accommodate deconvolution. The detectors of the preferred embodiment are rapidly tunable and self-modulating, not requiring the use of a notch or pass filter known in the art. Instead, the rapidly tunable characteristic of the detectors permits the image to be scanned across the pre-selected bands of approximately twelve in number in sufficient time to enable the data to be processed in parallel by the computer and to have an image generated describing the distribution of infrared emitted flux across the 4–15 μm range for each pixel of the image. The use of narrow band segment detection of infrared flux enables artifacts such as fluorescence, reflectivity, and environmental factors affecting the emitted flux of the surface of interest, as shown in FIGS. 3B–E, to be isolated and accounted for when determining actual temperature, reflectivity and fluorescence. Accordingly, the present apparatus and method for determining actual temperature for diagnostic purposes does not suffer from the inaccuracies of the prior art "black body" model single band detector systems and produces results sufficiently accurate for use in diagnosis of certain pathologies or diseases evidenced by spatial or temporal changes in actual skin temperature. Moreover, the present invention, on account of the capability of continuous modulation and detection of the area of interest is able to generate a time dependent image used, for example, to evaluate the rate of absorption of topical agents on the skin or frequencies of thermoregulatory processes. Accordingly, the detected data may be analyzed using mathematical means for extracting rates and frequencies such as Fourier analysis representing the detected data and generated image in rate or frequency form. The invention, therefore, is not limited to a mere "snapshot" of the image, but rather, is able to continuously display in real time the area of interest and generated images of the same.

MODIFICATIONS OF THE INVENTION

Although the preferred embodiment and a secondary embodiment of the invention are described in the specification and drawings herein, the invention contemplates still further modifications. For example, the invention may be practiced with the use of alternative filtering means such as stacked filters or other rapidly tunable embodiments adapted to scan across pre-selected segment widths of the 4-15 μm band.

It is also contemplated by the invention that two-dimensional arrays of increased size may be employed to further enhance the resolution of the images generated by the method and apparatus of the invention.

Still another modification of the invention may be use of the described method and apparatus for applications outside the scope of the determination of skin or surface temperature; e.g., for use as a tracking device or security device through the detection of fluorescent aberrations attendant to infrared flux emissions of a surface or calorimetry of biological or other processes in minute samples.

The invention also contemplates the use of various computing means and deconvolution algorithms, all of which are known and appreciated by one of skill in the art, to determine from the detected data the parameters of interest.

I claim:

1. An apparatus for determining temperature, reflectivity (or emissivity) and fluorescence of an area of interest from the detection of emitted infrared flux, comprising:

infrared detection means adapted to measure emitted infrared flux of said area in the 4-15 μm spectrum, said detection means being further adapted to be modulated over a plurality of pre-selected narrower spectral segments and to measure said emitted infrared flux in said segments over said 4-15 μm spectrum for each unit of said area of interest, said detection means further comprising a plurality of detectors arranged in a pre-selected configuration for detecting said emitted infrared flux in parallel over said narrower spectral segments for each portion of said area;

computing means, operatively communicating with said detector means and adapted to deconvolute the measured detected infrared flux for each pixel of said area to numeric values for temperature, fluorescence and reflectivity, said computing means further adapted to generate images of the deconvoluted temperature, reflectivity and fluorescence for said area of interest;

whereby, detection of infrared flux across an area of interest through spectral segments enables deconvolution of the detected data to accurately measure temperature, fluorescence and reflectivity (or emissivity).

2. The apparatus according to claim 1 wherein said detector means is a 256×256 focal plane array of tunable infrared flux detectors.

3. The apparatus according to claim 2 wherein said detectors are comprised of tunable Putley detectors.

4. The apparatus according to claim 1 wherein said detector means is adapted to detect emitted infrared flux in said preselected spectral segments of from 1 to 3 μm and wherein said preselected spectral segments number is at least 5.

5. The apparatus according to claim 1 wherein said computing means is a digital computer adapted to deconvolute said detected data using a series of algorithms describing temperature, reflectivity and fluorescence of the surface of interest as a function of the temperature of a black body emitter, the wavelength dependence of emissivity of the area, the temperature of the surrounding environment, the wavelength of light of the environment, the wavelength of exciting photons of fluorescence, and the wavelength of the fluorescent emission.

6. The device according to claim 1 wherein said detection means further comprises a plurality of black body reference emitters operatively arranged at the periphery of the field of view and means for maintaining said black body emitters at a constant, known temperature.

7. The apparatus according to claim 1 wherein said detection means comprises a 256×256 focal plane array of wide-band infrared detectors modulated by and communicating with filter means for detecting emitted infrared flux in said pre-selected spectral segments.

8. The apparatus according to claim 7 wherein said filter means is a continuously tunable acousto-optical filter.

9. The device according to claim 7 wherein said filter means is a rotatable sector disk of fixed band width infrared filters and wherein said multi-sectors number is at least 5.

10. The method for determining temperature, fluorescence and reflectivity (or emissivity) of a surface of interest through detection and measurement of emitted infrared flux, comprising the steps of:

providing detecting means adapted to measure emitted infrared flux for each unit of said surface in the 4-15 μm wavelength band;

providing modulating means adapted to selectively modulate said detecting means over a plurality of pre-selected spectral segments across said 4-15 μm wavelength band and wherein said plurality of pre-selected spectral segments is at least 5 in number;

detecting through the use of said detecting means the value of emitted infrared flux of each pixel of said surface for each of said pre-selected spectral segments;

providing a series of algorithms as a function of temperature of an ideal black body emitter, wavelength of emissivity of said surface, temperature of the surrounding environment, wavelength of the light of the environment, wavelength of exciting photons of fluorescence, and wavelength fluorescent emission, the solution of which determines temperature, reflectivity (or emissivity) and fluorescence of said surface;

providing computing means adapted to communicate with said detecting means and to deconvolute said emitted infrared flux into temperature, fluorescence and reflectivity for each of said pixels of said surface through the use of the provided algorithms;

generating an image of the distribution of said deconvoluted values of temperature, reflectivity (or emissivity) and fluorescence for said surface of interest.

11. The method according to claim 10 wherein the provided computing means is a digital computer adapted to solve said algorithms and to generate said image of temperature, fluorescence and reflectivity (or emissivity) and the temporal values thereof.

12. The method according to claim 10 wherein the provided detection means is a 256×256 focal plane array of tunable infrared flux detectors.

13. The method according to claim 10 wherein said detecting means comprises a two-dimensional focal plane array of tunable infrared detectors adapted to be modulated over at least 5 spectral segments.

14. Method according to claim 10 wherein said spectral segments are of between 1-3 μm.

15. The method according to claim 10 wherein the provided detecting means comprises a two-dimensional focal plane array of wide-band infrared detectors modulated by and communicating with a filter means for detecting emitted infrared flux in said pre-selected spectral segments.

16. The method according to claim 15 wherein said filter means is a continuously tunable acousto-optical filter.

17. The method according to claim 15 wherein said filter means is a rotatable multi-sector set of fixed band infrared filters.

* * * * *